United States Patent [19]

Haskell

[11] 4,024,028
[45] May 17, 1977

[54] EXTRACTIVE DISTILLATION OF HYDROCARBON MIXTURES

[75] Inventor: Donald M. Haskell, Bartlesville, Okla.

[73] Assignee: Phillips Petroleum Company, Bartlesville, Okla.

[22] Filed: Sept. 8, 1976

[21] Appl. No.: 721,260

[52] U.S. Cl. .................................. 203/51; 203/57; 203/58; 203/62; 203/78; 203/84; 203/73; 260/677 A; 260/681.5 R
[51] Int. Cl.² ...................... B01D 3/40; C07C 7/08; C07C 11/16
[58] Field of Search .................. 203/54, 51, 57, 58, 203/62, 38, 78, 84, 73; 260/681.5, 677 A

[56] References Cited
UNITED STATES PATENTS

| | | | |
|---|---|---|---|
| 2,360,859 | 10/1944 | Evans et al. | 208/325 |
| 2,434,424 | 1/1948 | Morris et al. | 203/52 |
| 2,455,803 | 12/1948 | Pierotti | 203/51 |
| 2,750,435 | 6/1956 | Fetchin | 203/51 |
| 2,816,943 | 12/1957 | Delaplaine | 203/62 |
| 3,350,282 | 10/1967 | Davis et al. | 203/58 |
| 3,350,283 | 10/1967 | Makin et al. | 203/62 |
| 3,716,620 | 2/1973 | Deschamps et al. | 423/228 |
| 3,898,135 | 8/1975 | Tidwell et al. | 203/58 |

*Primary Examiner*—Wilbur L. Bascomb, Jr.

[57] ABSTRACT

Hydrocarbons having different degrees of saturation are separated by extractive distillation using selective solvent comprising a mixture of dimethylsulfone, methylethylketone and sulfolane.

13 Claims, 1 Drawing Figure

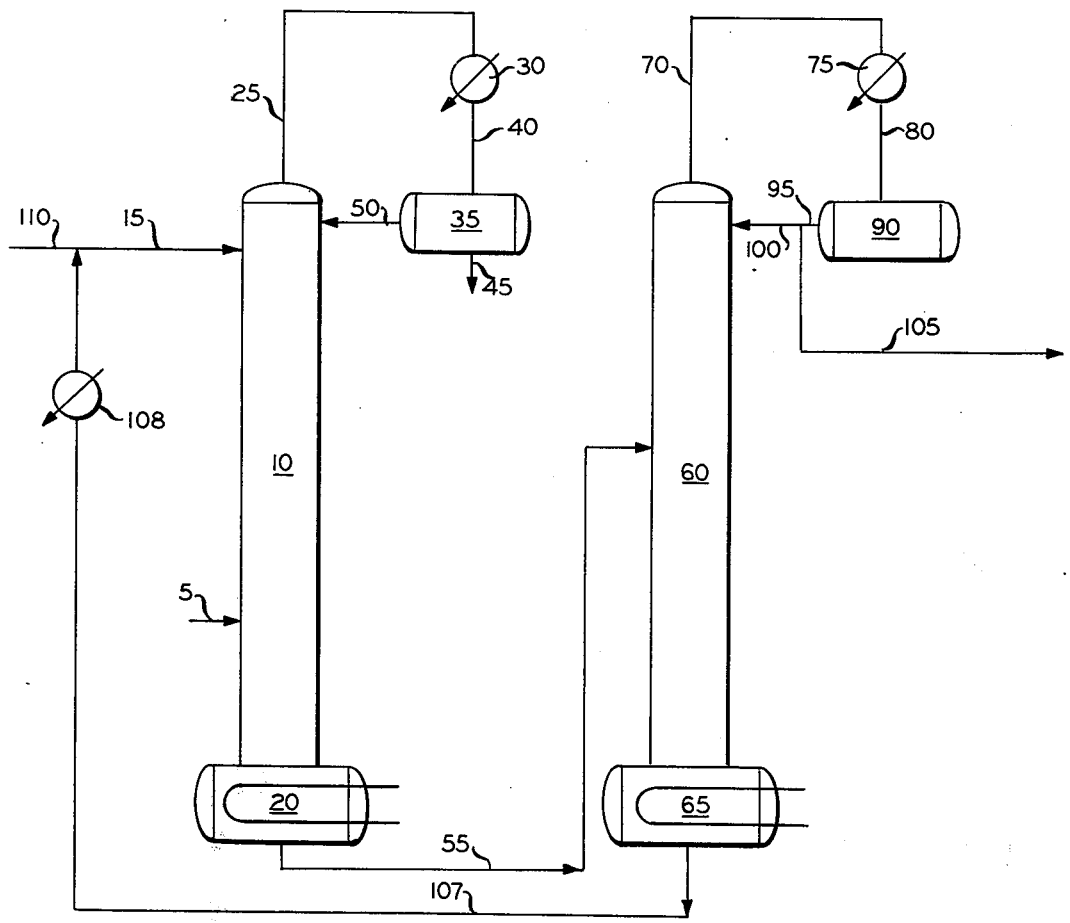

EXTRACTIVE DISTILLATION OF HYDROCARBON MIXTURES

Background of the Invention

This invention relates to a separation process. In particular, it relates to separation of hydrocarbons having different degrees of saturation by extractive distillation.

Mixtures containing components of similar vapor pressures or components which tend to form azeotropes with one another are impossible to separate by simple distillation. Methods such as azeotropic distillation solvent extraction, adsorption on solids and extractive distillation have been proposed to achieve separation of these mixtures.

One separation which has caused considerable difficulty, is the separation of a mixture composed of hydrocarbons having different degrees of unsaturation. To separate mixtures of such hydrocarbons, a third component, a selective solvent, is added to the mixture to alter the relative volatility of the original constituents thus permitting their separation. The selective solvent is usually of low volatility and is not appreciably vaporized in the fractionator. The selection of the solvent for a particular system is the crucial task in extractive distillation processes.

The present invention provides a solvent for extractive distillation of hydrocarbons having different degrees of saturation. Thus, one object of the invention is to provide an improved process for separation of hydrocarbons having different degrees of saturation.

Another object of the invention is to provide a process for extractive distillation of hydrocarbons having different degrees of saturation which utilizes less energy than the prior art processes.

A further object of the invention is to provide a process for separation of hydrocarbons having different degrees of saturation, which has an increased feed capacity thereby a lower equipment cost.

Still another object of the invention is to provide a novel selective solvent for the process of extractive distillation of hydrocarbons which differ in degrees of saturation.

A still further object of the invention is to provide a process for the extractive distillation of butene and butadiene mixtures which minimizes the concentration of trans-butene-2 and thus simplifies the final separation.

Other objects of the invention will become apparent to those skilled in the art upon studying this disclosure.

Summary of the Invention

In accordance with one aspect of the invention, a selective solvent comprising a mixture of dimethylsulfone, methylethylketone, and sulfolane is employed to separate by extractive distillation hydrocarbons having different degrees of unsaturation.

In accordance with another aspect, a solvent comprising 300 to 1,000 weight percent of the hydrocarbon feed is utilized in a fractionation zone to separate the feed comprising a mixture of four-carbon hydrocarbons having different degrees of saturation. The solvent incudes about 2–25 weight percent of dimethylsulfone, about 15–50 weight percent of methylethylketone and about 25–85 weight percent of sulfolane. The mixture together with the solvent are subjected to such extractive distillation conditions as to separate it into an overhead comprising mainly more saturated four-carbon hydrocarbons and bottoms comprising essentially solvent and less saturated four-carbon hydrocarbons. From the extractive distillation column the column overhead is withdrawn as a column overhead stream and the column bottoms withdrawn as column bottoms stream is passed to a stripper wherein $C_4$ hydrocarbons are taken off as stripper overhead and the solvent is withdrawn as stripper bottoms.

In accordance with still another aspect of the invention, a mixture of butenes and butadiene is introduced into an extractive distillation zone together with a ternary solvent comprising by weight about 2–25% of dimethylsulfone, about 15–50% of methylethylketone, and about 25–85% of sulfolane. The distillation column is maintained at such operating conditions including temperature and pressure that the feed is separated into a column overhead comprising mainly butenes and bottoms comprising mainly butadiene and solvent. The column overhead stream is recovered as essentially butenes, and the column bottom stream is passed to a stripper wherein it is subjected to such conditions as to separate it into butadiene taken off as stripper overhead and solvent removed as stripper bottoms.

Other aspects of the invention will become apparent to those skilled in the art upon studying this specification and appended claims.

Brief Description of the Drawing

The FIGURE depicts the flow diagram used in one embodiment of the process of this invention.

Detailed Description of the Invention

Surprisingly, it was discovered that use of about 300–1,000 weight percent of selective solvent comprising by weight about 2–25% of dimethylsulfone, about 15–50% of methylethylketone, and about 25–85% of sulfolane with the feed mixture comprising hydrocarbons having different degrees of unsaturation allows separation of the mixture by an extractive distillation process. The preferred solvent composition includes by weight 10% dimethylsulfone, 30% methylethylketone, and 60% sulfolane. Since the solvent's selectivity is generally a function of the degree of unsaturation, the mixtures can contain any combination of hydrocarbons as long as the hydrocarbons which are sought to be separated from the other hydrocarbon or other hydrocarbons differ in the degree of unsaturation. Both two-component and multi-component mixtures can be separated using the solvent of this invention. The feed to the extractive distillation column can also contain minor amounts of other hydrocarbons such as ethane, ethylene, propane, and propylene without adversely affecting the operation of the system.

The operating conditions of the column vary considerably depending on several factors including the constituents of the mixture to be separated, the desired degree of separation, the number of trays in the column, and the composition of the selective solvent; however, the usual operating conditions fall within the following ranges:

|  | Extractive Distillation Column | Stripper |
|---|---|---|
| Pressure Range: | | |
| psia | 75 – 115 | 60 – 95 |
| kPa | 517 – 792 | 413 – 655 |

-continued

|  | Extractive Distillation Column | Stripper |
|---|---|---|
| Temperatures at the Top: | | |
| ° F | 100 – 130 | 100 – 130 |
| ° C | 38 – 54 | 38 – 54 |
| Reflux Ratio, R/F (weight) | 2 – 5 | 1 – 3 |

The kettle temperatures will depend on the solvent composition, but for most applications these are about 200°–260° F (93°–127° C) for the extractive distillation column (bottom of the fractionation zone) and 280°–340° F (138°–171° C) for the stripper (bottom of the stripping zone).

It is estimated that at high solvent/feed ratios (more than about 7) and high reflux ratios (more than about 3) the minimum number of theoretical stages is about 30.

When the preferred solvent composition (10 weight percent dimethylsolfone, 30 weight percent methylethylketone, and 60 weight percent sulfolane) is used, the usual operating conditions are as follows:

|  | Extractive Distillation Column | Stripper |
|---|---|---|
| Pressure Range: | | |
| psia | 85 – 105 | 60 – 85 |
| kPa | 585 – 723 | 413 – 585 |
| Temperatures at the Top: | | |
| ° F | 120 – 125 | 105 – 110 |
| ° C | 49 – 52 | 41 – 43 |
| Reflux Ratio, R/F (weight) | 2 – 3 | 1 – 2 |

The kettle temperatures are about 230°–250° F (110°–121° C) for the extractive distillation column (bottom of the fractionation zone) and 315°–325° F (157°–163° C) for the stripper (bottom of the stripping zone). If butadiene is one of the components of the mixture which is introduced into the column, the temperature of the column should be at a conventiently low level to minimize polymerization of butadiene during the distillation; however, it must be above the level at which selective solvent precipitates which at atmospheric pressure is 55° F (13° C) for 10/30/60 mixture and 65° F (18° C) for 15/30/50 mixture of dimethylsulfone, methulethylketone, and sulfolane.

The practice of the invention will be further described by reference to a specific system depicted in the FIGURE. Referring now to the FIGURE, the mixture of hydrocarbons differing in the degree of unsaturation is introduced by 5 to the extractive distillation column 10. The solvent is fed near the top of the extractive distillation column 10 by 15 to assure its presence in high concentration upon most of the trays. The solvent alters the relative volatility of the original constituents, allowing separation of the feed into overhead comprising the more saturated hydrocarbon or hydrocarbons of the mixture and bottoms comprising essentially the least saturated hydrocarbon of the mixture and the solvent. By "more saturated" it is means that the hydrocarbon is more saturated relative to another hydrocarbon or hydrocarbons present in the mixture. Similarly, "least" or "less saturated" is a relative term comparing the satruation of a particular hydrocarbon to another hydrocarbon or hydrocarbons present in the mixture. The distillation conditions which must be maintained to permit the separation include proper temperature which is achieved by heat from the column reboiler 20 and proper pressure. The column overhead stream is withdrawn from the extractive distillation column 10 via 25 and passed into column condenser 30. From column cocdenser 30 the condensed column overhead stream is passed to the accumulator 35 via 40. A part of the overhead stream containing the least unsaturated hydrocarbons of the mixture is withdrawn from the accumulator 35 by 45 and a part thereof is returned as column reflux to the extractive distillation column 10 by 50.

The column bottoms stream is withdrawn from the extractive distillation column 10 by 55 and fed to the mid-section of the stripper 60. The operating conditions in the stripper 60, including temperature and pressure, are such as to separate the feed into stripper overhead comprising essentially the less saturated hydrocarbons recovered in stream 55 and stripper bottoms comprising essentially denuded solvent. The necessary heat is supplied to the stripper 60 by a reboiler 65. The stripper overhead is withdrawn from the stripper 60 by 70 and directed therefrom to stripper condenser 75 which cools the stripper overhead stream 70 before it is passed to the accumulator 90 via line 80. The liquid from the accumulator 90 leaving by 95 is subdivided into a stripper reflux stream 100 and a product stream 105. The recycle solvent stream 107 after cooling by cooler 108 is combined with the fresh solvent makeup stream 110 to form solvent feed stream 15.

The following example is included for illustrative purposes only and is not intended to limit in any way the scope of the invention.

EXAMPLE

In this example runs were made using a 4-inch (0.1 m) inside diameter extractive distillation column (EDC) with 140 trays. The EDC consisted of two 70-tray sections equipped with sieve trays. Each tray had six holes [0.515 inch (0.0131 m) diameter] for 10% hole area and a downcomer with an inside area occupying 9% of the total tray area. Tray spacing was 8 inches (0.203m). The solvent stripper column was 4-inch (0.1 m) inside diameter with 40 feet (12.2 m) of 5/8-inch (0.0159 m) pall ring packing. The flow diagram for the system is similar to that depicted in the FIGURE.

The feed for the test run contained the following ingredients in specified concentrations (analyzed by Gas-Liquid Chromatography):

| Component | Weight % |
|---|---|
| Ethane + Ethylene | 0.02 |
| Propane | 0.39 |
| Propylene | 0.61 |
| Isobutane | 0.54 |
| n-Butane | 9.64 |
| Butene-1 + Isobutylene | 35.12 |
| trans-Butene-2 | 7.58 |
| cis-Butene-2 | 5.77 |
| 1,3-Butadiene | 40.33 |
| Total | 100.00 |

The following three solvents were used in different runs:
1. Furfural,
2. Acetone/Sulfolane (25/75 mixture by weight),
3. Dimethylsulfone - methylethylketone - sulfolane (10/30/60 mixture by weight).

The conditions for the runs were selected in accordance with statistical experimental design to obtain meaningful comparison of the solvents. The conditions of all runs were within the ranges of conditions for the preferred solvent specified on page 4 of this specification. The data collected from the experimental runs at selected conditions were analyzed using regression analysis. The following results were calculated using the following assigned values: product purity 99 wt.% (defined as butadiene concentration in the stripper overhead product on a butenes-2 free basis), feed rate 30 lbs/hr, feed composition 60 wt.% butadiene:

| Butadiene Recovery weight percent | 80 | 90 | 99 |
|---|---|---|---|
| Furfural | | | |
| S lbs/hr | 184 | 232 | 275 |
| kg/hr | 83.4 | 105.2 | 124.7 |
| S/F | 6.1 | 7.7 | 9.2 |
| T ° F | 226 | 236 | 244 |
| ° C | 108 | 113 | 118 |
| Acetone/Sulfolane | | | |
| S lbs/hr | 103* | 132* | 188 |
| kg/hr | 46.7 | 59.9 | 85.3 |
| S/F | 3.4 | 4.4 | 6.3 |
| T ° F | 195 | 205 | 222 |
| ° C | 91 | 96 | 105 |
| DMSO$_2$/MEK/Sulfolane | | | |
| S lbs/hr | 157* | 201 | 241 |
| kg/hr | 71.2 | 91.1 | 109.3 |
| S/F | 5.2 | 6.7 | 8.0 |
| T ° F | 239 | 245 | 250 |
| ° C | 115 | 118 | 121 |

*Extrapolation outside of experimental data range
Where:
S = Solvent feed rate, lbs/hr (kg/hr)
F = Hydrocarbon feed rate, lbs/hr (kg/hr)
T = EDC kettle temperature, ° F (° C)

These results indicate that at a butadiene recovery of 99 wt.%, the acetone/sulfolane solvent system required 31.6% less solvent circulation than furfural to make the same butadiene purity and the DMSO$_2$/MEK/sulfolane system requires 12.4% less solvent circulation than furfural. Over the range of 80 to 99 wt.% butadiene recovery, the average reduction in solvent circulation over furfural was 39.5 and 13.6% for the acetone/sulfolane and DMSO$_2$/MEK/sulfolane solvent systems, respectively. Stated another way, for a given solvent circulation rate, the hydrocarbon feed could be increased by the above-stated percentages over that of furfural for equal purity and recovery. The advantage of lower kettle temperature of the extractive distillation column for the acetone/sulfolane system over furfural was not obtained with the DMSO$_2$/MEK/sulfolane system. At a butadiene recovery of 90 wt.%, the differences in kettle temperatures of the extractive distillation column for the mixed solvents and furfural were −22° E (−12° K) for the acetone/sulfolane system and +6° F (+3° K) for the DMSO$_2$/MEK/sulfolane system. Over the range of 80 to 99 wt.% butadiene recovery, the average EDC kettle temperature differences from furfural were −28° F (+16° K) and +9° F (+5° K) for the acetone/sulfolane and DMSO$_2$/MEK/sulfolane systems, respectively.

Although the acetone/sulfolane solvent requires the lowest solvent circulation rate for a given butadiene recovery, it has two deficiencies. The most serious one is that high volatility of acetone causes it to distill overhead with the butenes. Th problem can be partially solved by increasing the reflux ratio on the extractive distillation column, but the increased reflux ratio significantly increases utility requirements for the separation. Furthermore, a additional separation step is required for complete recovery of acetone from the raffinate overhead product, even at a increased reflux ratio. The separation step can include water washing of the raffinate overhead product, solvent extraction, or low pressure distillation.

The second deficiency of acetone/sulfolane, shared by furfural and many other selective solvents used for butadiene recovery, is the separation of trans-butene-2. It is common procedure to effect final butadiene purification by fractionation ot remove butene-2 isomers. Trans-butene-2 is the most difficult isomer to separate because its normal boiling point is only 9.5° F (5.3° K) higher than that of butadiene. It has been discovered that the DMSO$_2$/MEK/sulfolane solvent is much more efficient in separating trans-butene-2 than the other solvents tested. A series of runs was made, using the same equipment and conditions within ranges specified in the application, to determine this relative efficiency. The smoothed data from the series of runs summarized below, shows the concentration of trans-butent-2 in the butadiene extract product as a function of butene-1 concentration in that product for the selective solvents tested:

| Weight percent of butene-1 in the extract product (105) | 0.2 | 0.6 | 1.0 |
|---|---|---|---|
| Weight percent of trans-butene-2 in the extract product (105) when using as solvent: | | | |
| Furfural | 4.4 | 5.3 | 6.2 |
| Acetone/Sulfolane | 2.4 | 4.0 | 5.7 |
| DMSO$_2$/MEK/Sulfolane | 1.2 | 2.4 | 3.7 |

The data indicate that with DMSO$_2$/MEK/sulfolane as a selective solvent at different levels of butene-1, the extract product contained 27%, 45% and 59% of trans-butene-2 contained therein when furfural was used as a selective solvent and 50%, 60%, and 55% when acetone/sulfolane was used as a selective solvent. I claim:

1. A process for separation of a feed mixture of hydrocarbons having different degrees of unsaturation which comprises:
    introducing the feed mixture and a selective solvent mixture comprising sulfolane, methylethylketone and dimethylsulfone into a fractionation zone having a top and a bottom and therein subjecting said mixtures to extractive distillation conditions including such pressure and corresponding temperature to separate the mixtures into a column overhead containing substantially all relatively saturated hydrocarbons and column bottoms containing mainly relatively unsaturated hydrocarbons and solvent mixture; and
    withdrawing a column overhead stream containing substantially all relatively satruated hydrocarbons, and a column bottoms stream containing mainly relatively unsaturated hydrocarbons and said selective solvent.

2. A process as claimed in claim 1 wherein the feed mixture comprises hydrocarbons containing four carbon atoms.

3. A process as claimed in claim 1 wherein the relatively saturated hydrocarbon is butene-1 and the relatively unsaturated hydrocarbon is butadiene.

4. A process as claimed in claim 3 wherein the concentration of selective solvent mixture is in the range from about 300 to about 1000 percent by weight of the hydrocarbon feed.

5. A process as claimed in claim 4 wherein the concentration of dimethylsulfone in the selective solvent mixture is in the range from about 2 to about 25 percent by weight, th concentration of methylethylketone in said mixture is in the range from about 15 to about 50 percent by weight, and the concentration of sulfolane is in the range from about 25 to about 85 percent by weight.

6. A process as claimed in claim 5 wherein the pressure in the fractionation zone is in the range from about 75 psia (517 kPa) to about 115 psia (792 kPa) and the temperature at the top of the fractionation zone is in the range from about 100° F (38° C) to about 130° F (54° C) and in the bottom of the fractionation zone from about 200° F to about 260° F (93° C—127° C).

7. A process as claimed in claim 6 further comprising:
cooling the column overhead stream; and
returning such a portion of the cooled column overhead stream to the fractionation zone as column reflux as to maintain the weight ratio between column reflux and feed mixture in the range from about 2 to about 3.

8. A process as clamed in claim 1 further comprising:
passing the column bottoms stream into a stripping zone having a top and a bottom;
maintaining the conditions in the stripping zone includng temperature and pressure to separate the bottoms stream introduced thereto into a stripper overhead containing substantially all hydrocarbons and a stripper bottoms containing mainly denuded solvent; and
allowing stripper overhead to exit as stripper overhead stream and stripper bottoms as stripper bottoms stream.

9. A process as claimed in claim 8 wherein the pressure in the stripping zone is in the range from about 60 to about 95 psia (413–655 kPa) and temperature at the top of the stripping zone is in the range from about 100°–130° F (38–54° C) and in the bottom of the stripping zone from about 280° F to about 340° F (110°–121° C).

10. A process as claimed in claim 9 further comprising:
cooling the stripper overhead stream; and
returning such a portion of the cooled stripper overhead stream to the stripping zone as stripper reflux as to maintain the weight ratio between column reflux and column bottoms stream in the range from about 1 to aboutb 2.

11. A process as claimed in claim 4 wherein the concentration of dimethylsulfone in the selective solvent mixture is about 10 weight precent, the concentration of methylethylketone in said mixture is about 30 weight percent, and the concentration of sulfolane in said mixture is about 60 weight percent.

12. A process as claimed in claim 1 wherein the feed mixture comprises butadiene, butene-1 and trans-butene-2.

13. A process as claimed in claim 8 wherein the feed mixture comprises butadiene, butene-1 and trans-butene-2.

* * * * *